United States Patent
Jiménez Castro

(10) Patent No.: US 11,963,934 B2
(45) Date of Patent: Apr. 23, 2024

(54) FLOW VALVE FOR USE WITH ENTERAL FEEDING PUMP FLUSH MODULE

(71) Applicant: Zevex, Inc., Salt Lake City, UT (US)

(72) Inventor: Pablo A. Jiménez Castro, Concepcion (CR)

(73) Assignee: Zevex, Inc., Salt Lake City, UT (US)

( * ) Notice: Subject to any disclaimer, the term of this patent is extended or adjusted under 35 U.S.C. 154(b) by 260 days.

(21) Appl. No.: 17/331,809

(22) Filed: May 27, 2021

(65) Prior Publication Data
US 2022/0378666 A1    Dec. 1, 2022

(51) Int. Cl.
*A61J 15/00*    (2006.01)

(52) U.S. Cl.
CPC ....... *A61J 15/0088* (2015.05); *A61J 15/0076* (2015.05); *A61J 15/0092* (2013.01)

(58) Field of Classification Search
CPC ...... A61M 5/16827; A61M 2005/1403; A61M 2202/0482; A61M 39/223; F16K 11/08; F16K 11/083; F16K 11/0833; F16K 11/0836; F16K 11/085; F16K 11/0853; F16K 11/0856; F16K 11/087; F16K 11/0873; F16K 11/0876
See application file for complete search history.

(56) References Cited

U.S. PATENT DOCUMENTS

| | | | |
|---|---|---|---|
| 3,957,082 A | 5/1976 | Fuson et al. | |
| 5,584,671 A | 12/1996 | Schweitzer et al. | |
| 6,626,884 B1 * | 9/2003 | Dillon | A61B 5/150366 604/323 |
| 7,896,859 B2 | 3/2011 | Daly | |
| 9,699,816 B2 | 7/2017 | Harr et al. | |
| 2011/0022762 A1 | 1/2011 | Waldhoff et al. | |
| 2012/0085951 A1 * | 4/2012 | Ludwig | F16K 31/042 251/129.04 |
| 2014/0018746 A1 * | 1/2014 | Ueda | A61M 39/223 604/248 |

(Continued)

FOREIGN PATENT DOCUMENTS

WO    2005/115501 A2    12/2005

OTHER PUBLICATIONS

Covidien AG, Operating Manual—Kangaroo Joey Enteral Feed and Flush Pump with Pole Clamp, Programmable, Mar. 2020.

*Primary Examiner* — Nathan R Price
*Assistant Examiner* — Anh Bui
(74) *Attorney, Agent, or Firm* — Hodgson Russ LLP

(57) ABSTRACT

A docking station for removable connection to an enteral feeding pump enables automated flushing of an administration set loaded in the enteral feeding pump. The docking station may have a valve seat configured to receive a switchable flow valve of the administration set, a flush controller, an actuator connected to the flush controller and configured to releasably mate with the switchable flow valve when the switchable flow valve is received by the valve seat, and data communication means by which data signals sent by the enteral feeding pump are inputted to the flush controller of the docking station when the enteral feeding pump is connected to the docking station. In operation, the flush controller may receive a flush command sent by the enteral feeding pump and transmit a control signal to the actuator for switching the switchable flow valve to a flush position in response to the flush command.

2 Claims, 16 Drawing Sheets

FEED POSITION

(56) References Cited

U.S. PATENT DOCUMENTS

| | | |
|---|---|---|
| 2014/0053931 A1 | 2/2014 | Whitaker |
| 2015/0305073 A1 | 10/2015 | Harr et al. |
| 2018/0236168 A1 | 8/2018 | Holderle et al. |
| 2019/0314249 A1 | 10/2019 | Thompson et al. |
| 2020/0164141 A1* | 5/2020 | Biermann ............ A61M 5/1413 |

* cited by examiner

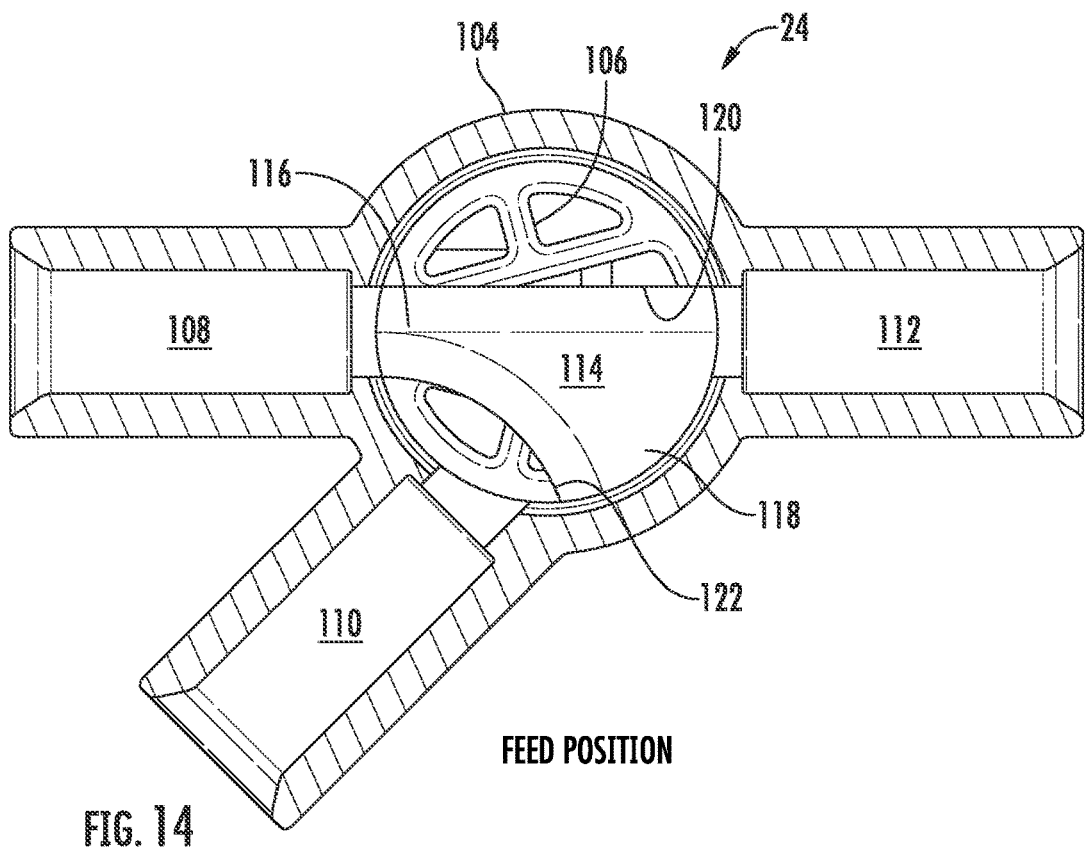
FIG. 14  FEED POSITION
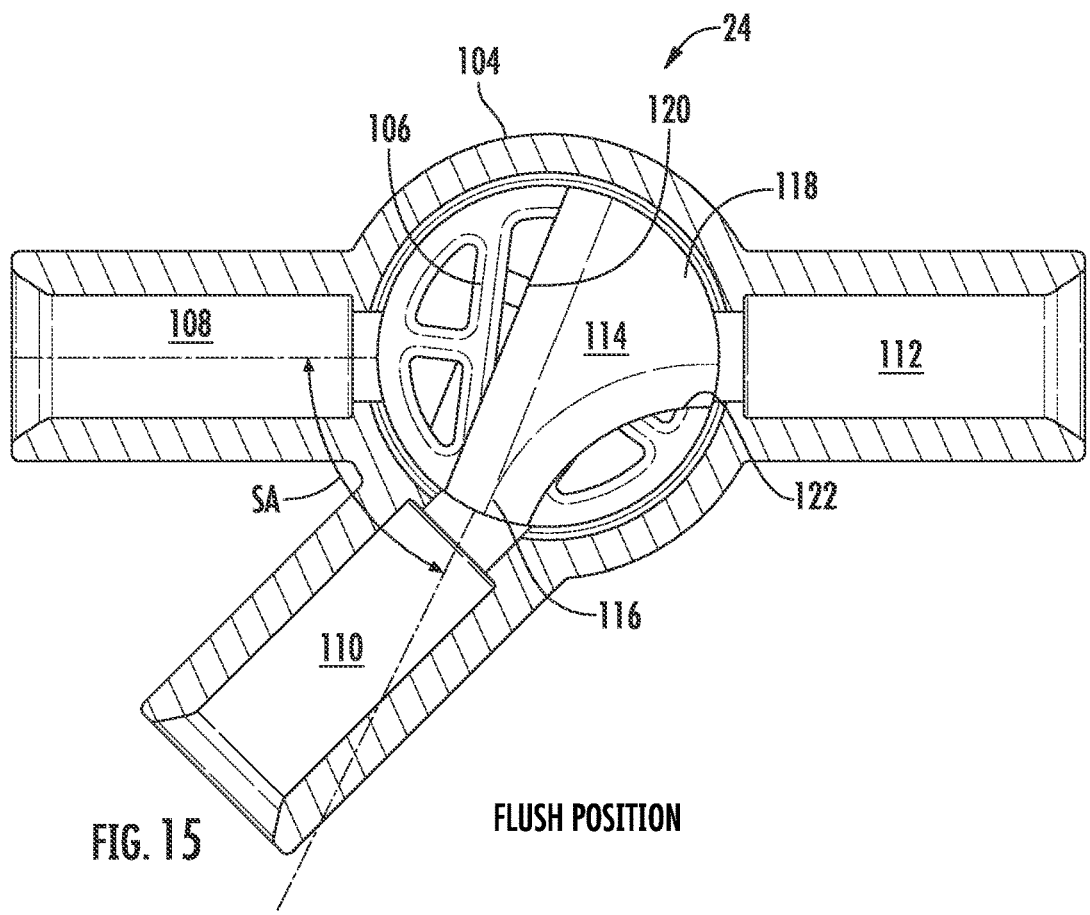
FIG. 15  FLUSH POSITION

FLOW VALVE FOR USE WITH ENTERAL FEEDING PUMP FLUSH MODULE

FIELD OF THE INVENTION

The present invention relates to a device and method for flushing an administration set with flushing liquid after the administration set is used to deliver nutritional liquid to a user.

BACKGROUND OF THE INVENTION

Programmable enteral feeding pumps are used to carry out controlled delivery of nutritional liquid to a user. In a common arrangement, an enteral feeding pump receives a disposable administration set comprising flexible tubing having a tubing segment designed to be engaged by a pumping mechanism of the enteral feeding pump. One end of the flexible tubing connects to a source of nutritional liquid, and the other end of the flexible tubing is arranged to deliver the nutritional liquid directly into the gastrointestinal tract of the user. Highly viscous nutritional liquids, for example mother's milk, tend to collect on the inner wall of the flexible tubing and clog the flow passageway. As a result, actual delivery of nutritional liquid to the user may be reduced relative to the prescribed or intended delivery.

It is known to flush administration set tubing by forcing a flushing liquid, such as water, to flow through the tubing. For example, a flushing operation may be recommended before and/or after a feeding operation is performed. Manual flushing may be carried out by positioning a syringe loaded with the flushing liquid at one end of the tubing, and injecting the flushing liquid into the tubing to flow through the tubing and flush nutritional liquid residue from the tubing. This type of manual flushing operation is laborious and requires that the administration set be disconnected from the pump, the source of nutritional liquid, and the user's feeding port or feeding tube.

Automated flushing apparatus are known, whereby the pumping mechanism of the enteral feeding pump is used to force flushing liquid through the tubing of the administration set. U.S. Pat. No. 7,896,859, taken together with international publication WO 2005/115501, describes an apparatus wherein the administration set has a feed tubing branch and a flush tubing branch merged at a switchable flow valve into a pump tubing portion. The feed tubing branch is connected to a source of nutritional liquid, whereas the flush tubing branch is connected to a source of flushing liquid. The pump tubing portion and the flow valve are loadable into a programmable enteral feeding pump which includes a motorized valve actuator for switching the flow valve among a feed position, a flush position, and a blocking position, whereby either nutritional liquid or flushing liquid may be selected for pumping through the pump tubing portion or no flow is permitted through the valve so that the valve may be unloaded from the pump. The disclosed apparatus adds weight and complexity to the enteral feeding pump, which is undesirable in pumps intended for ambulatory usage.

What is needed is an apparatus which facilitates flushing of an enteral feeding administration set without the drawbacks mentioned above.

SUMMARY OF THE INVENTION

The present disclosure provides a docking station for removable connection to an enteral feeding pump that enables automated flushing of an administration set loaded in the enteral feeding pump. The docking station may generally comprise a valve seat configured to receive a switchable flow valve of the administration set, a flush controller, an actuator connected to the flush controller and configured to releasably mate with the switchable flow valve when the switchable flow valve is received by the valve seat, and data communication means by which data signals sent by the enteral feeding pump are inputted to the flush controller of the docking station when the enteral feeding pump is connected to the docking station. In operation, the flush controller may receive a flush command sent by the enteral feeding pump and transmit a control signal to the actuator for switching the switchable flow valve to a flush position in response to the flush command.

A method of flushing tubing of an enteral feeding administration set according to the present disclosure may generally comprises the steps of connecting an enteral feeding pump to a docking station, connecting a flush tubing branch of the administration set to a source of flushing liquid, loading a pump tubing portion of the administration set in the enteral feeding pump, mating a flow valve of the administration set with an actuator of the docking station, receiving a user flush command, operating the actuator to move the flow valve to the flush position in response to the user flush command, and operating the enteral feeding pump to pump flushing liquid from the source of flushing liquid through the flush tubing branch, the flow valve, and the pump tubing portion. The flush command may be entered by the user by way of a user interface of the enteral feeding pump.

The disclosure further provides an enteral feeding pump system which may comprise an administration set, an enteral feeding pump, and a docking station. The administration set may include a feed tubing branch connectable to a source of nutritional liquid, a flush tubing branch connectable to a source of flushing liquid, a flow valve connected to the feed tubing branch and the flush tubing branch, and a pump tubing portion connected to the flow valve, wherein the flow valve has a feed position wherein the flow valve permits flow communication between the feed tubing branch and the pump tubing portion and prevents flow communication between the flush tubing branch and the pump tubing portion, and wherein the flow valve has a flush position wherein the flow valve permits flow communication between the flush tubing branch and the pump tubing portion and prevents flow communication between the feed tubing branch and the pump tubing portion. The enteral feeding pump may be configured to receive the pump tubing portion, and may include a pumping mechanism acting on the pump tubing portion to pump liquid through the pump tubing portion in a flow direction away from the flow valve. The docking station may include an actuator configured for mating with the flow valve, wherein the actuator is selectively operable to switch the flow valve between the feed position and the flush position when the flow valve is mated with the actuator.

The present disclosure also provides a switchable flow valve suitable for use with liquids having a relatively high viscosity. The flow valve generally comprises a hollow valve housing including a food entrance port, a flush entrance port, and an exit port, and a valve body received by the valve housing. The valve body may be rotatable about a valve axis relative to the valve housing, and the valve body may include a flow passage having an input end and an output end. A passage area of the output end of the flow passage may be greater than a passage area of the input end of the flow passage. The valve body may have a rotational feed position wherein the input end of the flow passage faces the food entrance port and the output end of the flow passage faces the exit port to enable communication between the food entrance port and the exit port through the flow passage. The valve body may also have a rotational flush position wherein the input end of the flow passage faces the flush entrance port and the output end of the flow passage faces the exit port to enable communication between the flush entrance port and the exit port through the flow passage. The flow passage may have a straight wall extending linearly from the input end to the output end and a curved wall diverging from the straight wall along a curved path from the input end to the output end.

BRIEF DESCRIPTION OF THE DRAWING VIEWS

The nature and mode of operation of the present disclosure will now be more fully described in the following detailed description taken with the accompanying drawing figures, in which.

Figure 6:
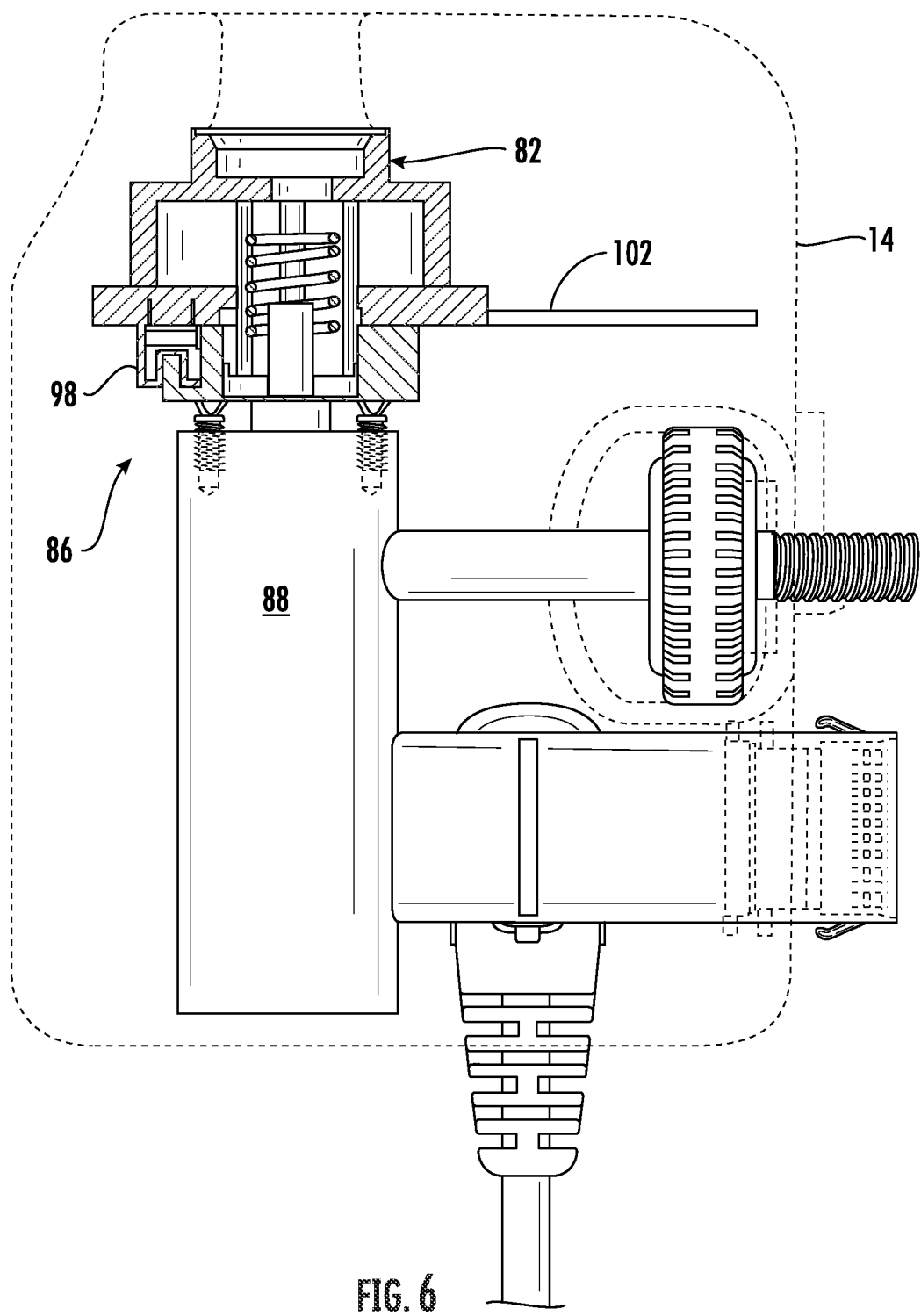
Figure 7:
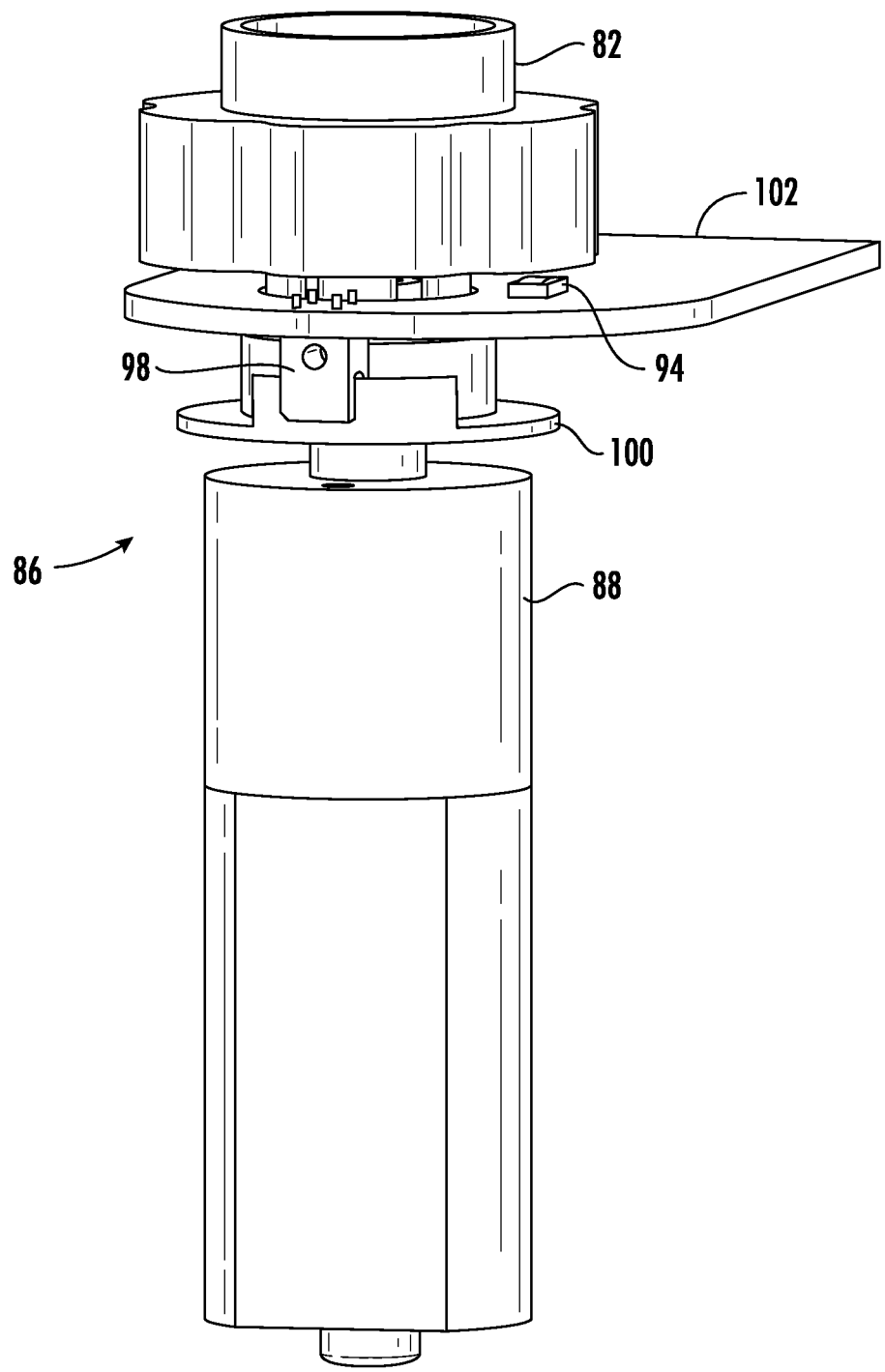
Figure 8:
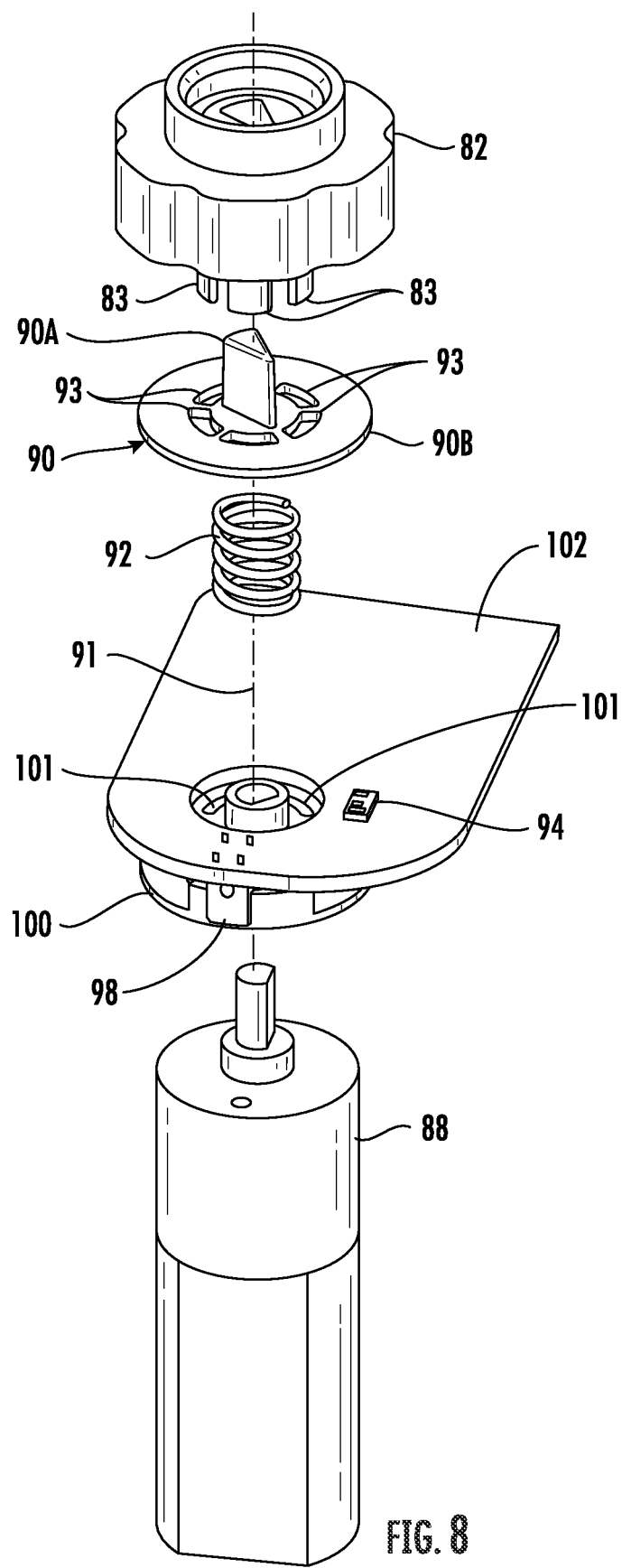
Figure 9:
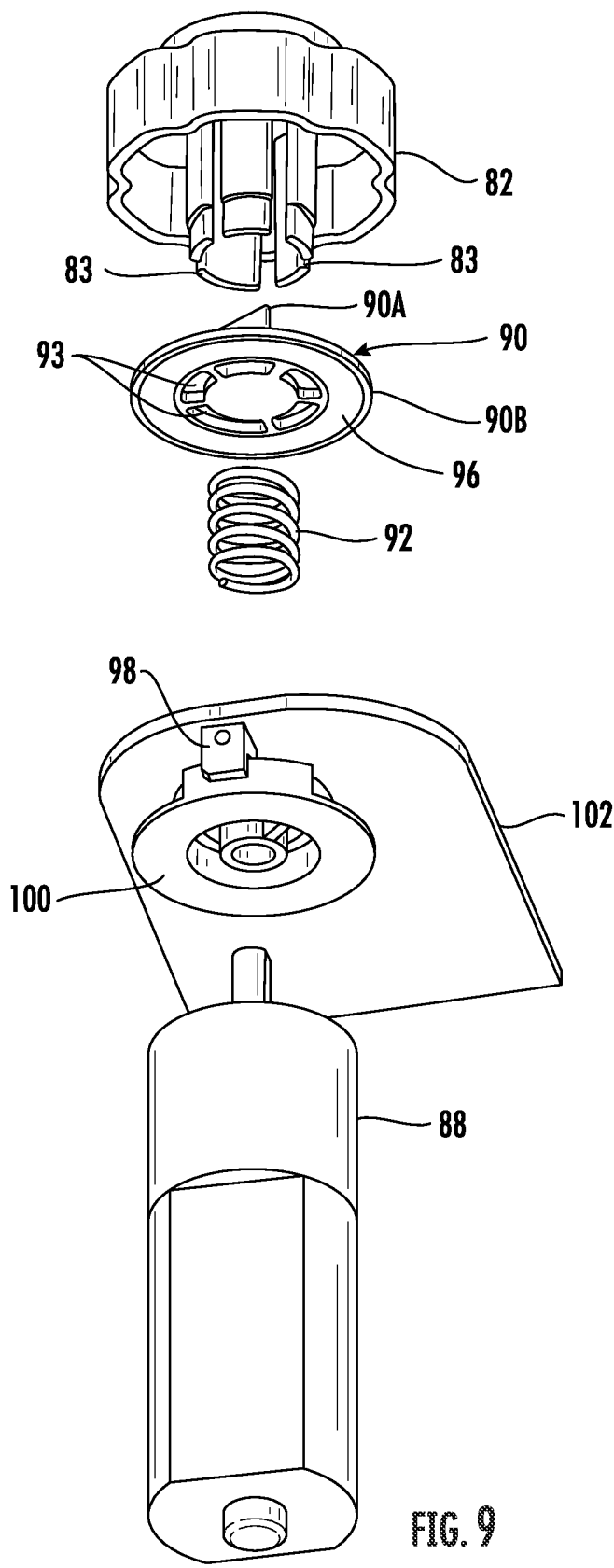
Figure 10:
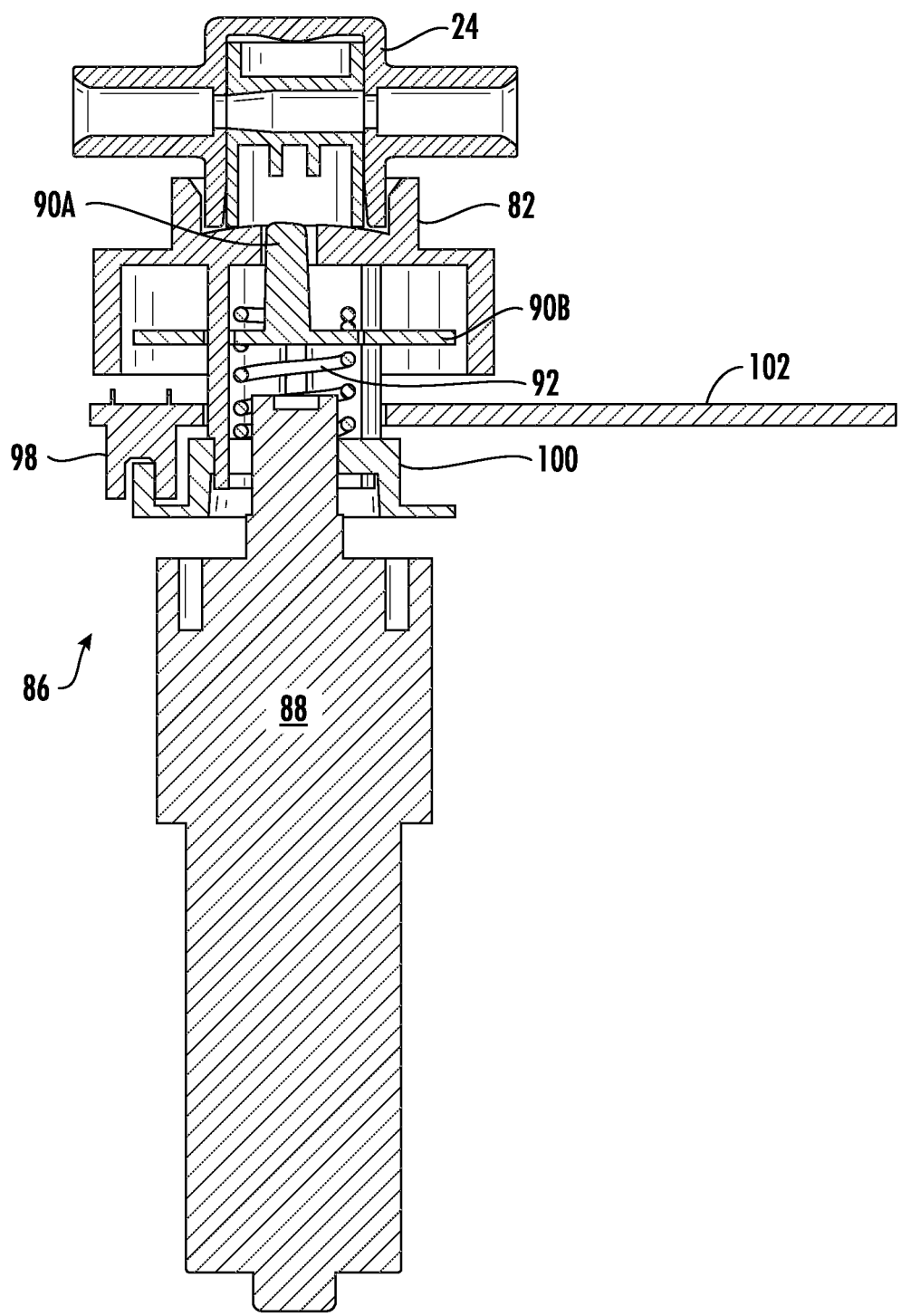
Figure 11:
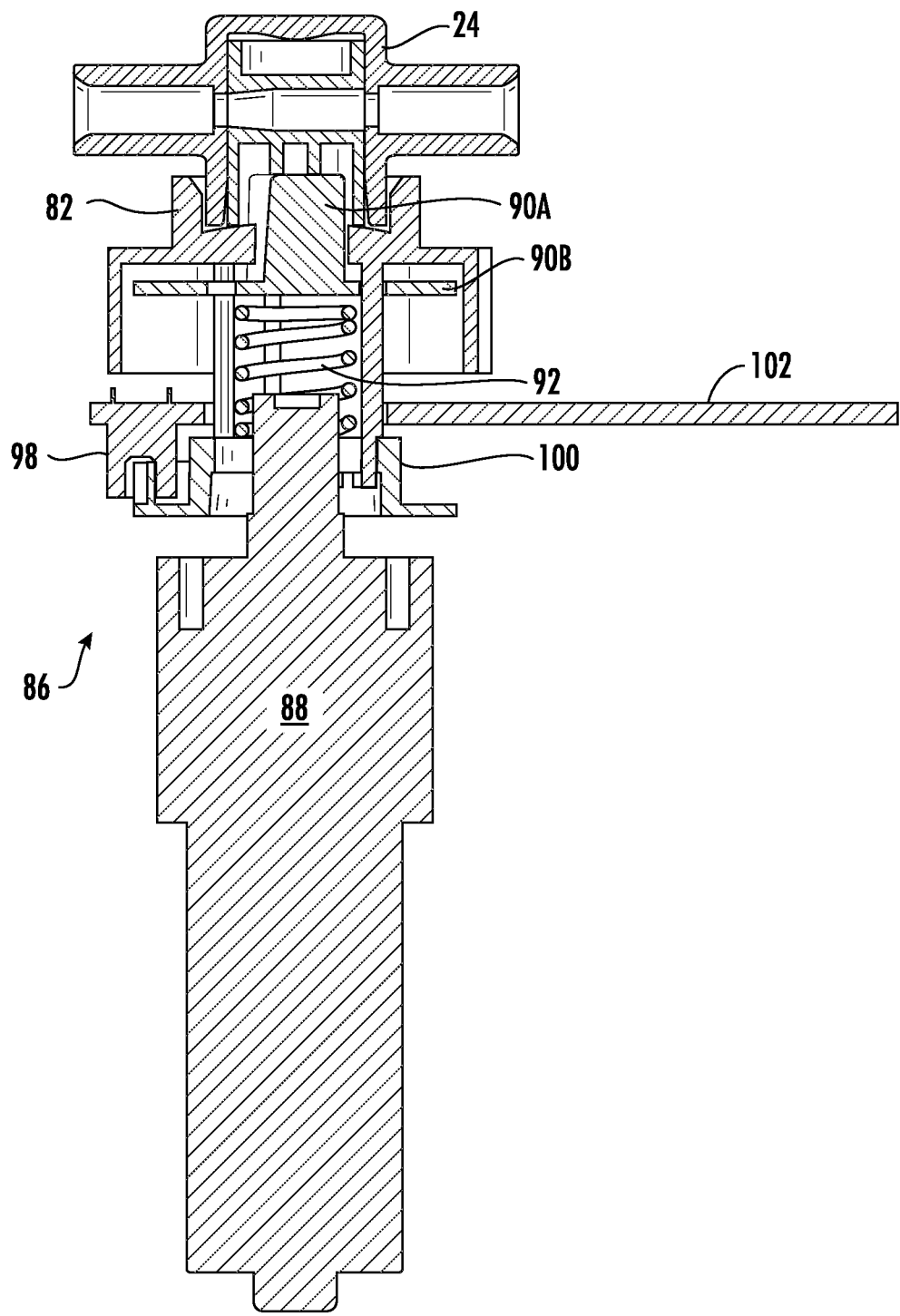
Figure 12:
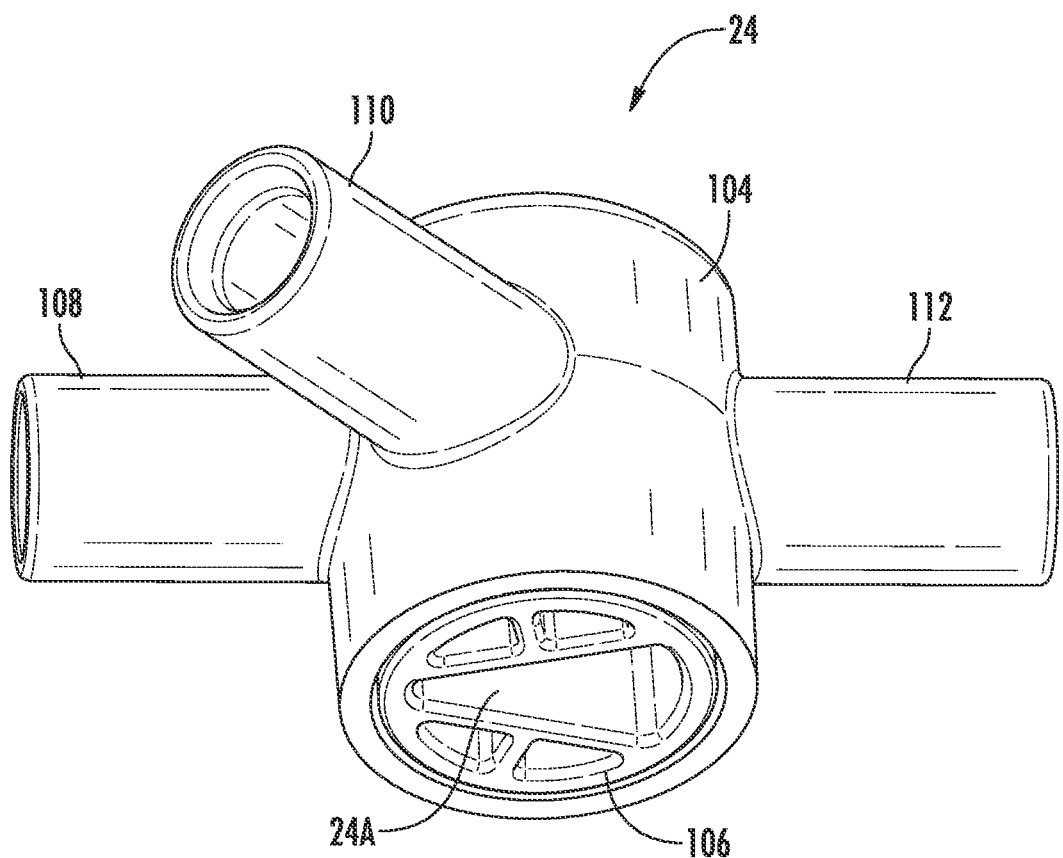
Figure 13:
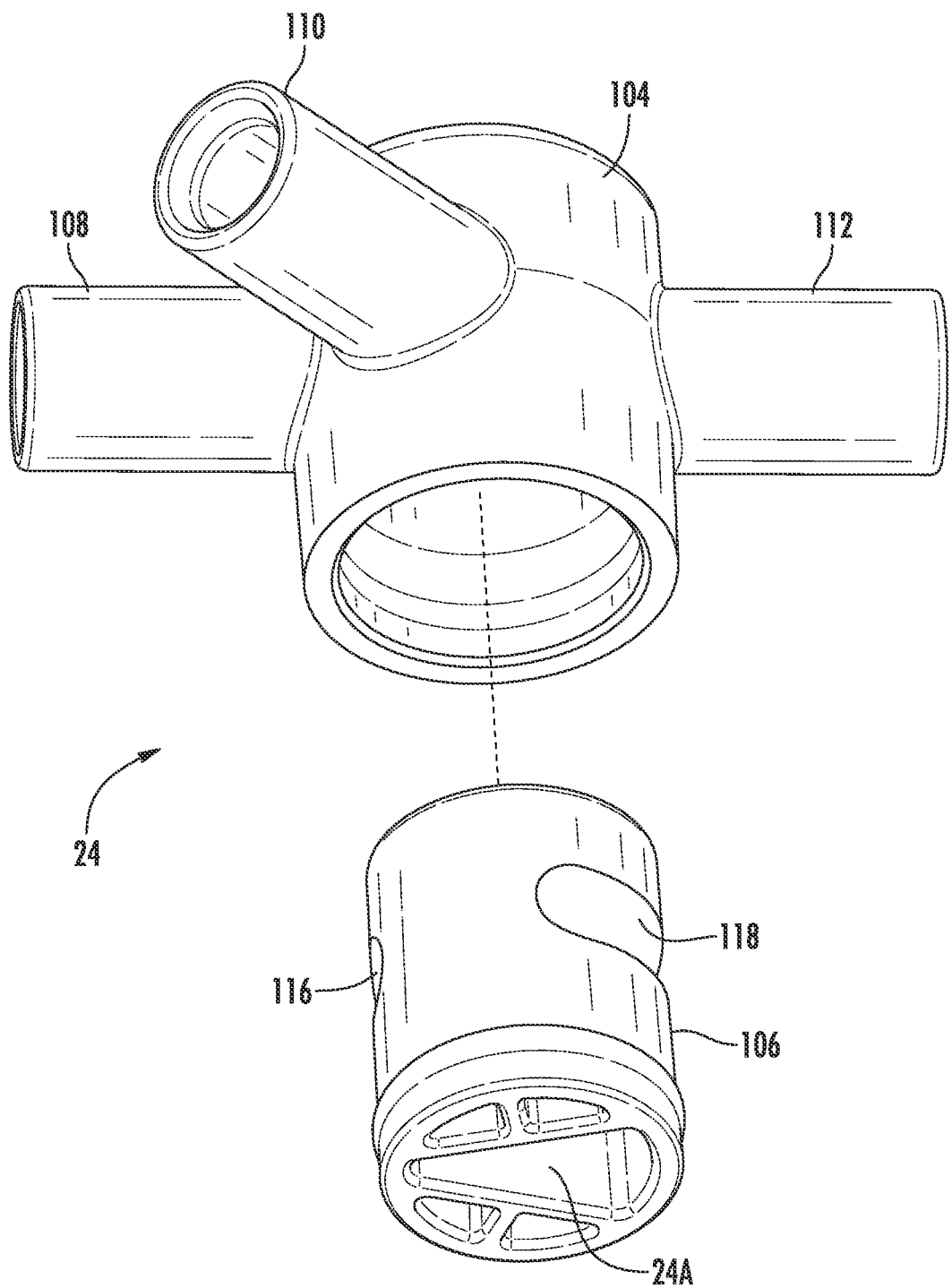
Figure 16:
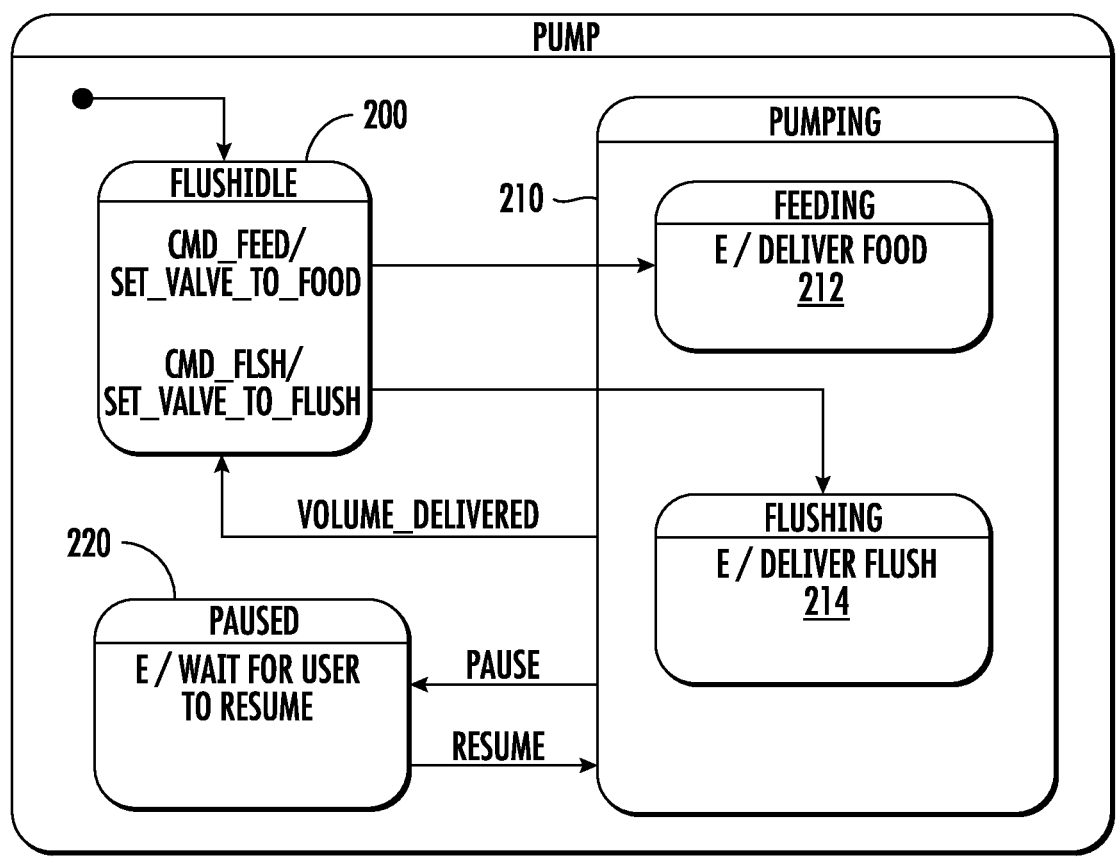
Figure 17:
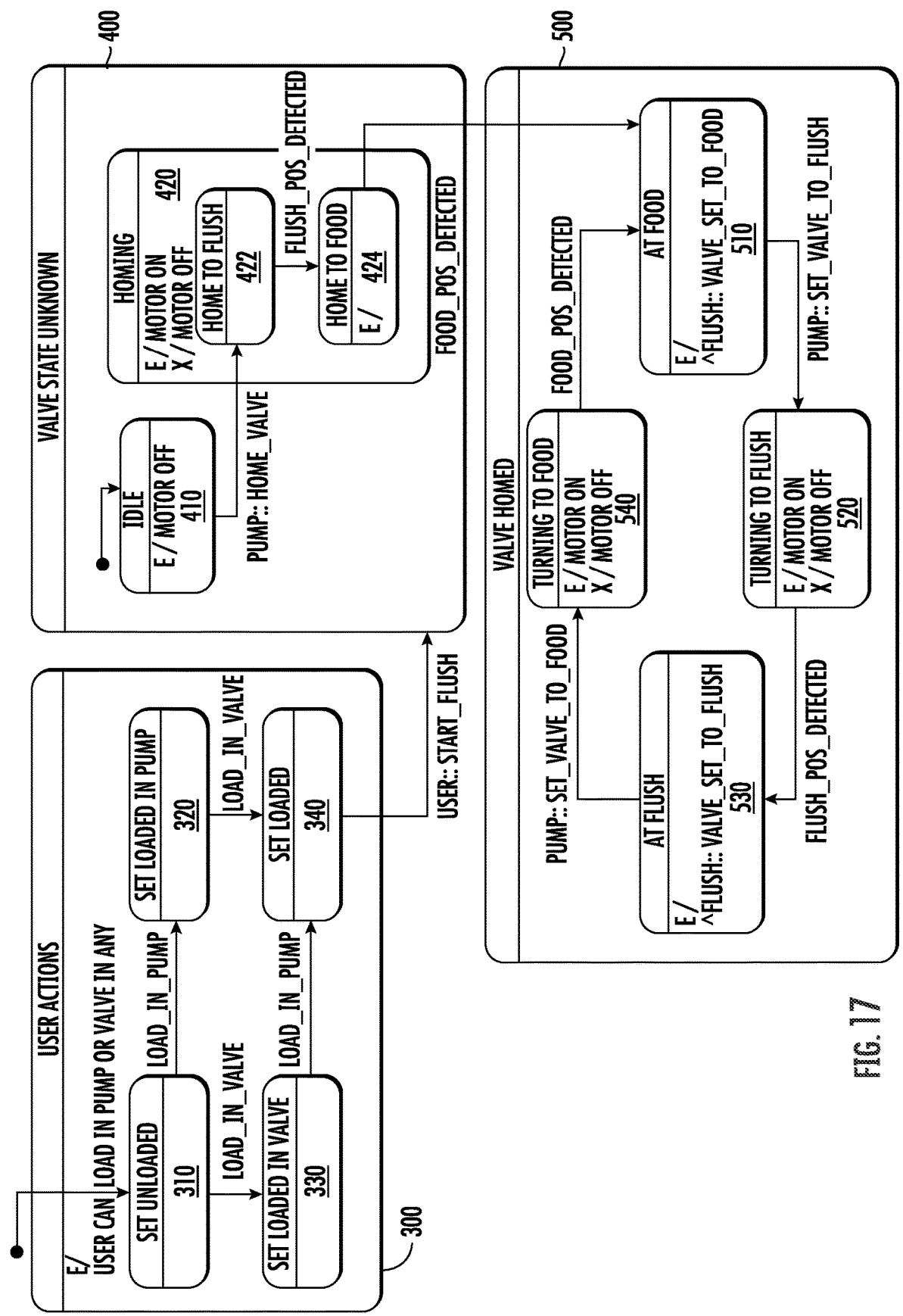

FIG. 6 a cross-sectional view of the docking station;

FIG. 7 is a perspective view of a valve actuator of the docking station;

FIG. 8 is an exploded perspective view of the valve actuator;

FIG. 9 is another exploded perspective view of the valve actuator;

FIG. 10 is a cross-sectional view showing a switchable flow valve of the administration set received in a valve seat of the docking station, wherein the flow valve is not yet mated with the valve actuator;

FIG. 11 is a view similar to that of FIG. 10, wherein the flow valve is mated with the valve actuator;

FIG. 12 is a perspective view of the flow valve:

FIG. 13 is an exploded perspective view of the flow valve;

FIG. 14 is a sectional view taken along the line 14-14 in FIG. 12 showing the flow valve in a feed position thereof;

FIG. 15 is a view similar to that of FIG. 14 but showing the flow valve in a flush position thereof;

FIG. 16 is a state diagram generally illustrating control of the infusion pump system by software in the enteral feeding pump in accordance with an embodiment of the disclosure; and FIG. 17 is another state diagram illustrating control of the infusion pump system to carry out a method of flushing tubing of the administration set in accordance with an embodiment of the disclosure.

DETAILED DESCRIPTION

Figure 1:
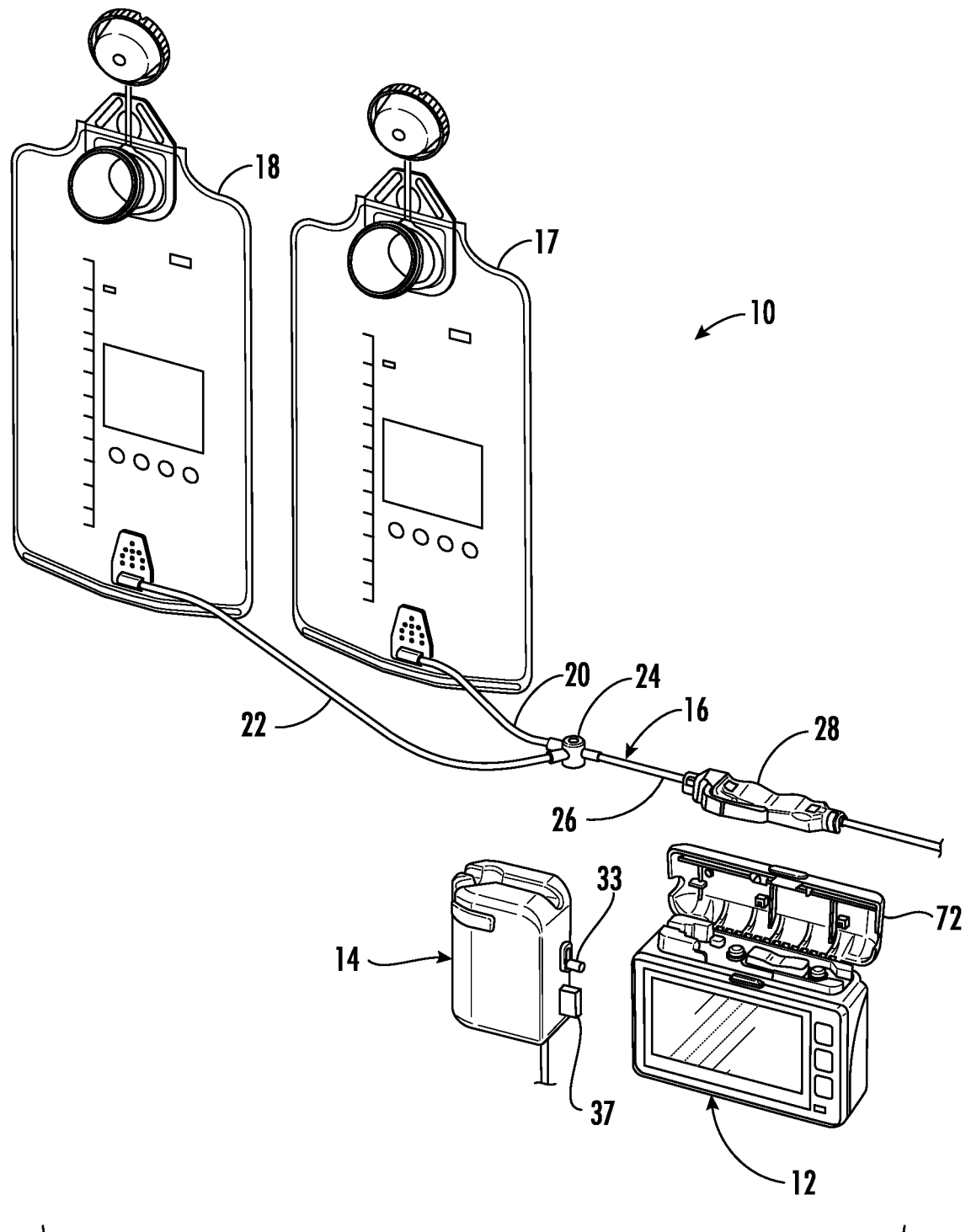
FIG. 1 is an exploded perspective view showing an enteral feeding pump system formed in accordance with an embodiment of the present disclosure.
Figure 2:
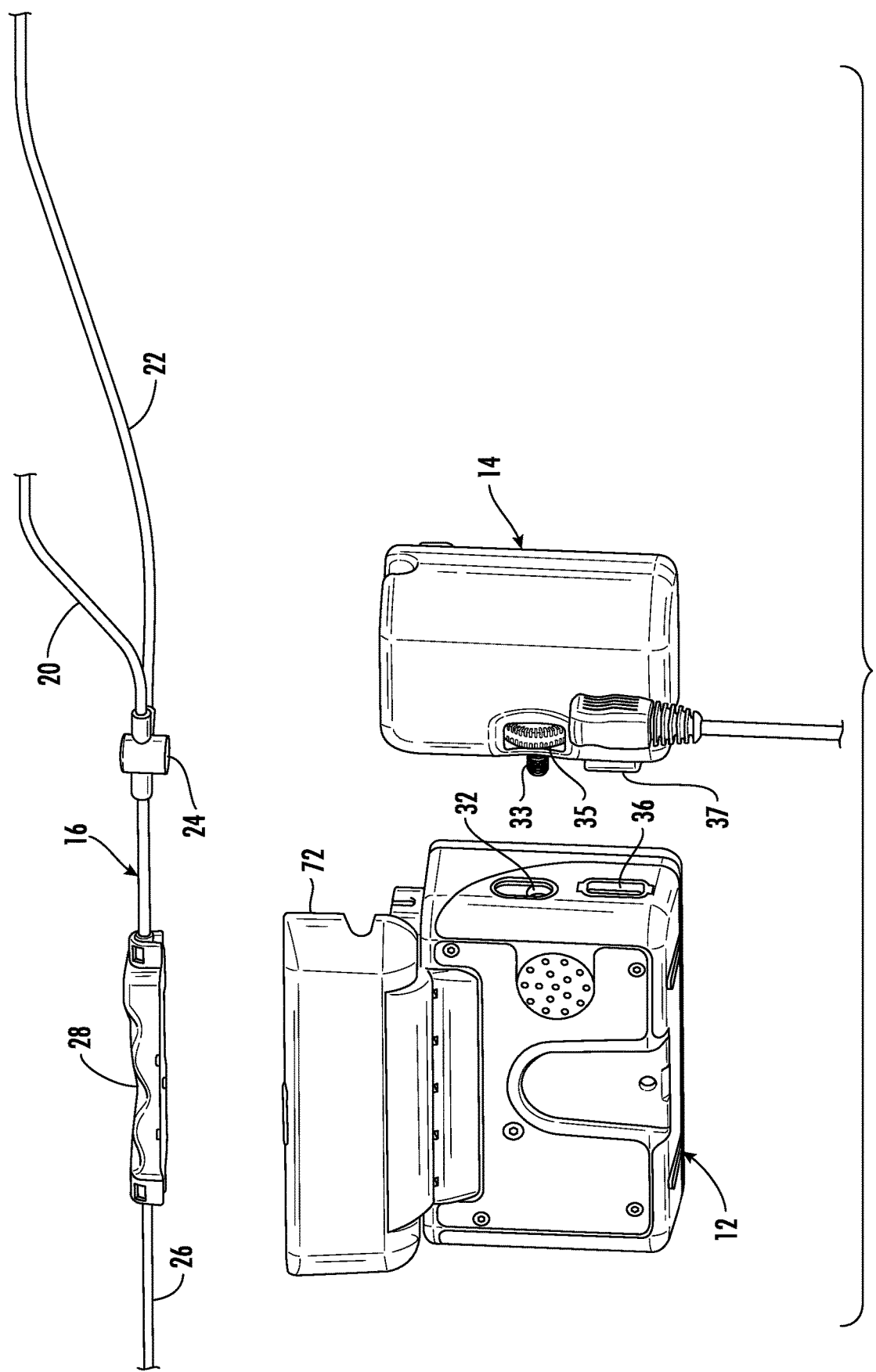
FIG. 2 is another exploded perspective view showing the enteral feeding pump system of FIG. 1 from a rear viewpoint, with sources of nutritional liquid and flushing liquid being omitted.

FIGS. 1 and 2 show and enteral feeding pump system 10 formed in accordance with an embodiment of the present disclosure. Enteral feeding pump system 10 generally comprises an enteral feeding pump 12, a docking station 14, and an administration set 16. System 10 may further comprise a source of nutritional liquid 17 and a source of flushing liquid 18. When enteral feeding pump 12 is connected to docking station 14, and administration set 16 is loaded in enteral feeding pump 12 and docking station 14 as described below, enteral feeding pump may be operated by a user to selectively carry out a feeding operation or a flushing operation. Docking station 14 may provide other functionality, for example recharging of batteries for powering enteral feeding pump 12, however the present disclosure concerns flushing functionality.

Administration set 16 may be configured to selectively allow feeding and flushing operations. Administration set 16 may include a feed tubing branch 20 connectable to nutritional liquid source 17, a flush tubing branch 22 connectable to flushing liquid source 18, a flow valve 24 connected to feed tubing branch 20 and flush tubing branch 22, and a pump tubing portion 26 connected to the flow valve 24. Flow valve 24 may have a feed position in which the flow valve permits flow communication between feed tubing branch 20 and pump tubing portion 26, and prevents flow communication between flush tubing branch 22 and pump tubing portion 26. Flow valve 24 may further have a flush position in which the flow valve permits flow communication between flush tubing branch 22 and pump tubing portion 26, and prevents flow communication between feed tubing branch 20 and pump tubing portion 26. Flow valve 24 is switchable between the feed and flush positions to selectively allow feeding and flushing operations.

Figure 3:
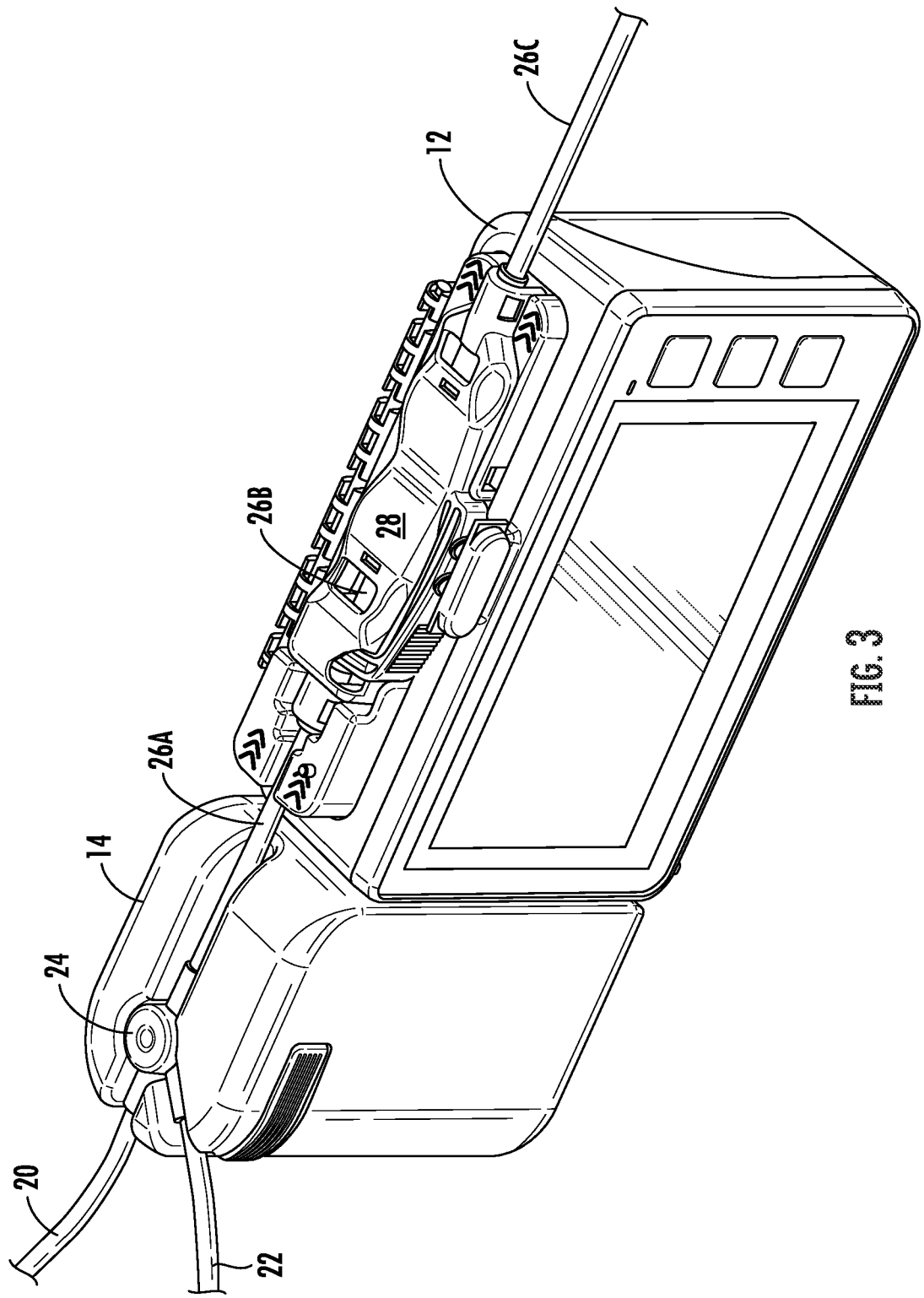
FIG. 3 is an unexploded perspective view showing an enteral feeding pump of the system connected to a docking station of the system, and an administration set of the system loaded in the enteral feeding pump and the docking station, wherein a door of the enteral feeding pump is omitted.
Figure 4:
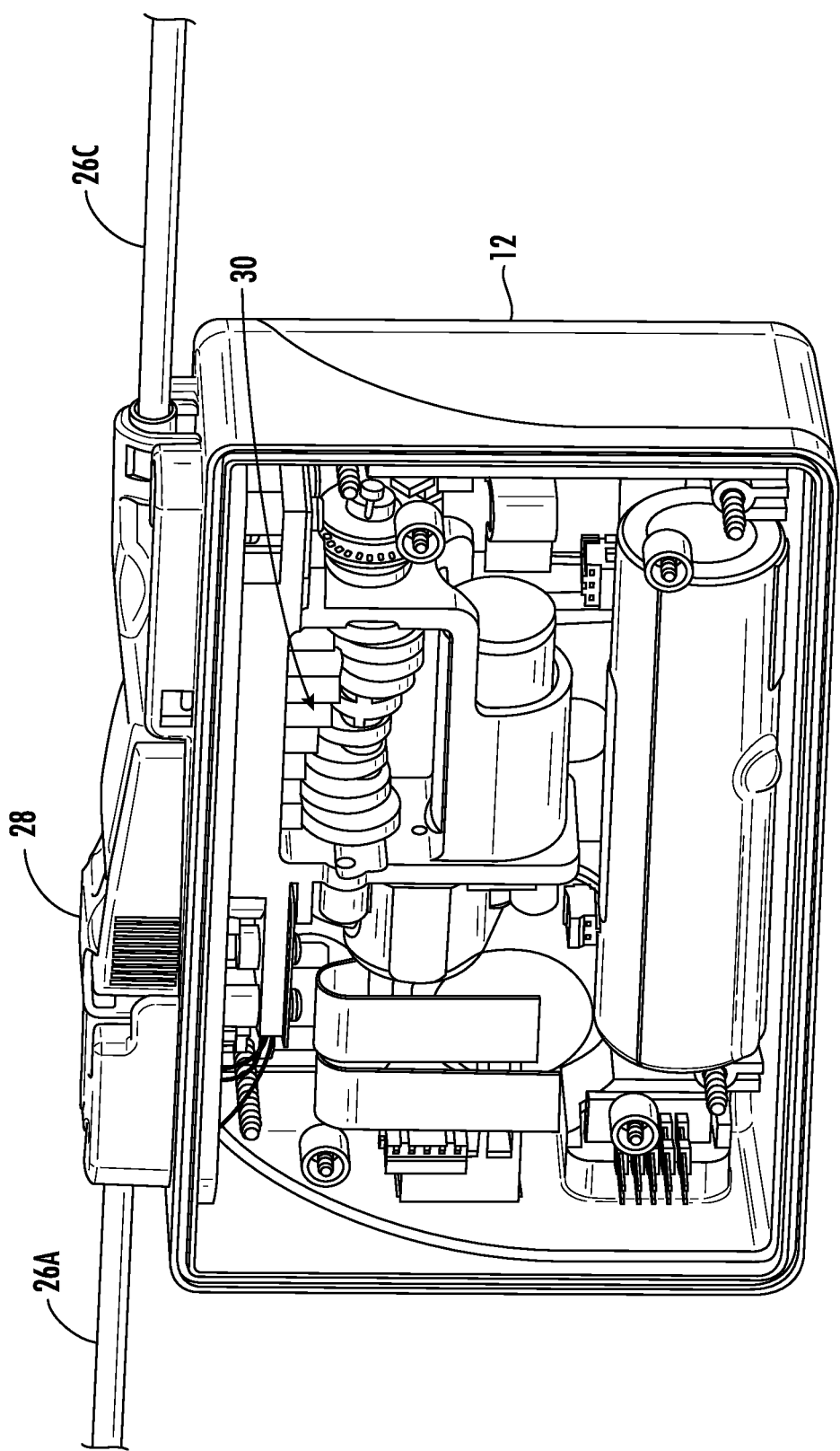
FIG. 4 is a perspective view of the enteral feeding pump wherein a front of the pump housing is removed to show internal structure of the pump.

Administration set 16 may include a cassette 28 for loading a segment of pump tubing portion 26 into enteral feeding pump 12. As illustrated in FIGS. 3 and 4, pump tubing portion 26 may have a pumping segment 26B arranged between an upstream segment 26A connected to flow valve 24 and a downstream segment 26C. As will be understood, downstream segment 26C may communicate with a patient or user during a normal feeding operation in which enteral feeding pump 12 is used to pump nutritional liquid from source 17 to the user through a feeding tube, for example a gastrostomy tube. Pumping segment 26B may be arranged to extend through cassette 28 and is positioned opposite a pumping mechanism 30 of pump 12 when cassette 28 is loaded in the pump. Pumping mechanism 30 acts on pumping segment 26B of pump tubing portion 26 to pump liquid through pump tubing portion 26 in a flow direction away from flow valve 24. Pumping mechanism 30 may be a linear peristaltic pumping mechanism as illustrated in FIG. 4, or may take other forms such as a rotary peristaltic pumping mechanism or a curvilinear peristaltic pumping mechanism.

Feed tubing branch 20, flush tubing branch 22, and upstream and downstream segments 26A and 26B of pump tubing portion 26 may be PVC tubing or other suitable tubing. Pumping segment 26B may be made of soft PVC, silicone, or other suitable material to resiliently deform when acted upon by pumping mechanism 30. An end of feed tubing branch 20 releasably connects to nutritional liquid source 17, and an end of flush tubing branch 22 releasably connects to flushing liquid source 18.

When nutritional liquid is pumped through administration set 16, the inner walls of the tubing may become lined with residual matter, particularly if the nutritional liquid has a high viscosity. As will be described in greater detail below, docking station 14 has an integrated flush module which interfaces with enteral feeding pump 12 and with flow valve 24 of administration set 16 to automatically configure system 10 to flush the tubing of administration set 16 with flushing liquid from source 18 to remove residual matter so that the administration set may continue to function in an efficient and accurate manner when more nutritional fluid is pumped through the administration set in a subsequent feeding operation.

Enteral feeding pump 12 and docking station 14 may include respective mechanical connection members to permit enteral feeding pump 12 to be securely but releasably connected to docking station 14. For example, enteral feeding pump 12 may have a nut 32 accessible through an opening in an end face of the pump housing for mating with a threaded stud 33 protruding from an opposing end face of the docking station housing. Threaded stud 33 may be manually rotatable relative to the docking station housing by means of a wheel or dial 35 as shown in FIG. 2.

Figure 5:
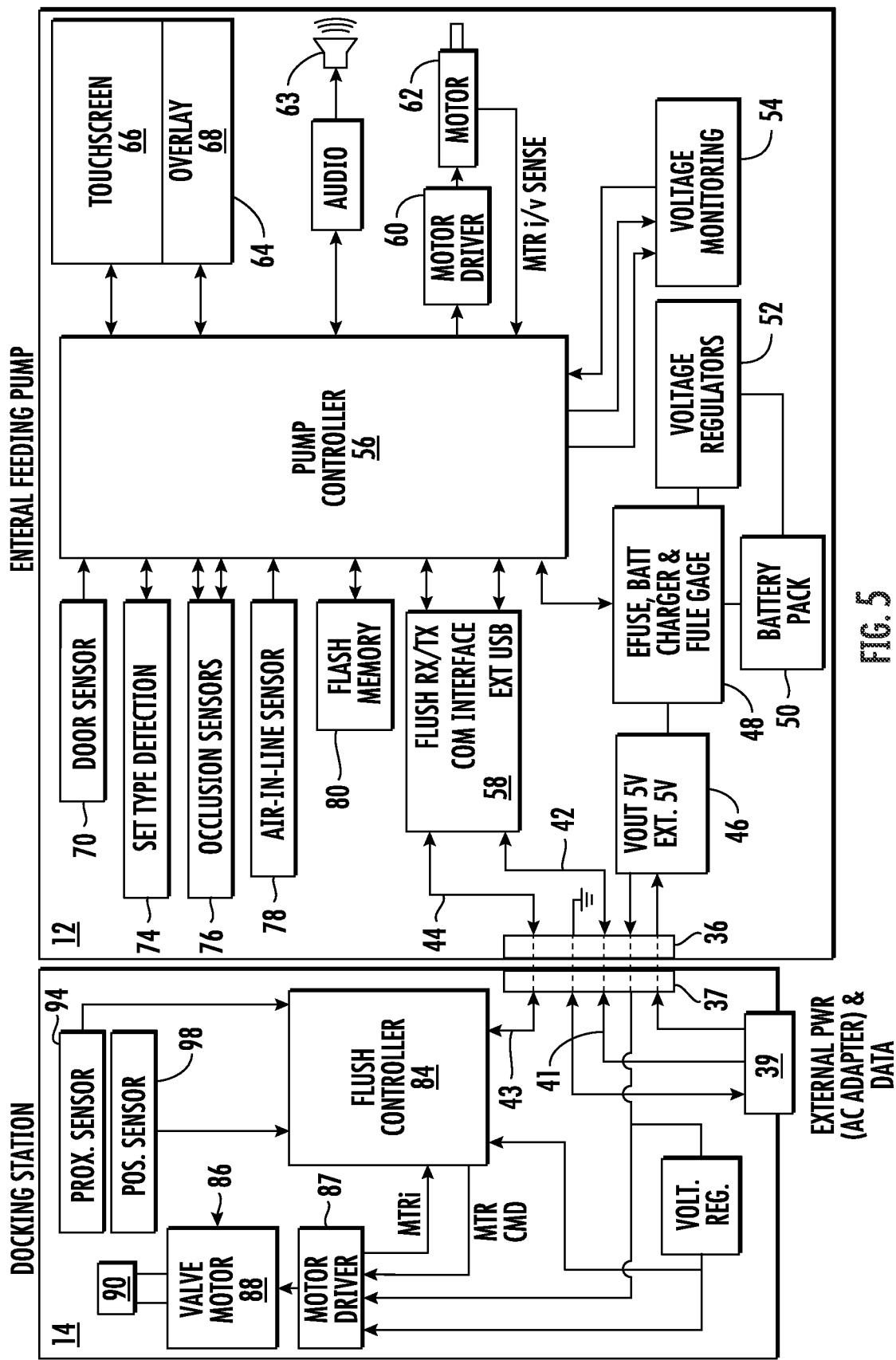
FIG. 5 is a schematic block diagram of the infusion pump and the docking station.

Reference is also made now to the schematic diagram of FIG. 5 to further describe enteral feeding pump 12 and docking station 14.

Enteral feeding pump 12 may include an electrical connection port 36 configured to releasably mate with a corresponding electrical connection port 37 on docking station 14 when enteral feeding pump 12 and docking station 14 are connected end-to-end as shown in FIG. 3. Electrical connection port 36 on enteral feeding pump 12 may include a configuration of connectors (e.g. pins and/or sockets), and electrical connection port 37 on docking station 14 may have a complementary configuration of connectors able to releasably mate with the connectors of port 36. Docking station 14 may further include an external power and data connection port 39 by which AC power and a USB may be connected to docking station 14. When the connectors of ports 36 and 37 are mated, external power is supplied from port 39 of docking station 14 to feeding pump 12, an output voltage is supplied from feeding pump 12 to docking station 14, a USB line 41 of docking station 14 is linked with a USB line 42 of feeding pump 12, and an internal data communication line 43 of docking station 14 is linked with an internal data communication line 44 of feeding pump 12. Enteral feeding pump 12 may include power supply and battery charging circuits 46 and 48, a battery pack 50, voltage regulators 52, and a voltage monitoring circuit 54 as shown for example in FIG. 5.

Enteral feeding pump 12 may also include a pump controller 56 acting as a central processing unit for pump 12. Pump controller 56 may include, for example, a digital microcontroller or a digital microprocessor and related circuitry. USB line 42 and data communication line 44 of feeding pump 12 may be connected to pump controller 56 through a communications interface 58. Pump controller 56 may be connected to a motor driver 60 arranged to drive a motor 62 of pumping mechanism 30. Pump controller 56 is programmed to send motor control commands to motor driver 60 to operate motor 62 such that pumping mechanism 30 delivers a desired flow rate of nutritional fluid to a user.

Pump 12 may have other components connected to pump controller 56, such as an audio speaker 63 providing audible signals to a user, and a user interface 64 including a touchscreen 66 and/or a control button overlay 68 for displaying information to a user and enabling a user to enter pump control commands and operating information. Pump 12 may also have various sensors connected to pump controller 56 for providing feedback signals related to pump operating status. Such sensors may include a door sensor 70 for detecting whether a door 72 of pump 12 is open or closed, a set type detector 74 configured to determine a type of administration set 16 currently loaded in the pump, occlusion sensors 76 arranged to detect occlusions in pump tubing portion 26 at locations upstream and downstream from pumping mechanism 30, and an air-in-line sensor 78 arranged to detect air bubbles in liquid conveyed through pump tubing portion 26. Pump 12 may also include one or more memory modules 80 connected to pump controller 56 or integrated onboard pump controller 56.

Docking station 14, further illustrated in FIG. 6, generally comprises a valve seat 82 configured to receive switchable flow valve 24 of administration set 16. Docking station 14 also comprises a flush controller 84, for example a digital microcontroller or a digital microprocessor and related circuitry, and an actuator 86 connected to the flush controller, wherein the actuator is configured to releasably mate with switchable flow valve 24 when the switchable flow valve is received by valve seat 82. As will be described in greater detail below, flush controller 84 is configured to send control signals to actuator 86 for switching flow valve 24 between its feed and flush positions.

When enteral feeding pump 12 is connected to docking station 14, data communication is enabled between pump controller 56 and flush controller 84. In the depicted embodiment, data communication line 43 of docking station 14 conveys data signals to and from flush controller 84. When enteral feeding pump 12 is connected to docking station 14, data communication line 44 of pump 12 is linked with data communication line 43 of the docking station, thereby establishing a hardwired connection for conveying data signals between pump controller 56 and flush controller 84. By way of non-limiting example, the data communication lines 43, 44 may be RS-232 data transmission lines. Instead of or in addition to using a hardwired connection, a wireless connection may be used. For example, a wireless signal transceiver may be linked to pump controller 56, and another wireless signal transceiver may be linked to flush controller 84, to enable wireless data communication between controllers 56 and 84.

An embodiment of actuator 86 is shown in detail in FIGS. 7-11. Actuator 86 may include an electric motor 88 and a coupler element 90 driven by motor 88 to rotate about a valve switching axis 91. Motor 88 may be operably connected to flush controller 84 by way of a motor driver circuit 87 as shown in FIG. 5. Coupler element 90 may be configured to mate with switchable flow valve 24 such that motor-driven rotation of coupler element 90 about valve switching axis 91 switches flow valve 24 between its feed and flush positions. Coupler element 90 may be configured to mate with switchable flow valve 24 only when coupler element 90 and flow valve 24 are in a single predetermined rotational orientation relative to one another about valve switching axis 91. Coupler element 90 may be linearly displaceable relative to motor 88 along valve switching axis 91 between a retracted position (FIG. 10) and an extended position (FIG. 11), wherein coupler element 90 mates with flow valve 24 when coupler element 90 is in the extended position and the coupler element and flow valve 24 are in the single predetermined rotational orientation. For example, a tip portion 90A of coupler element 90 and a corresponding recess 24A of flow valve 24 may have complementary shapes which permit tip portion 90A to fit within recess 24A only when coupler element 90 and flow valve 24 are in a single predetermined rotational orientation relative to one another about valve switching axis 91. In the figures, the complementary shape is that of a circular segment, however other shapes are possible, including but not limited to a triangle or a trapezoid. An irregular pattern of mating protrusions and recesses may also be used. Those skilled in the art will recognize that a male tip or protrusion may be provided either on coupler element 90 or on flow valve 24, and a mating female recess may be provided either on flow valve 24 or on coupler element 90. Coupler element 90 may further include a radially enlarged flange portion 90B from which tip portion 90A extends.

Coupler element 90 may be spring biased toward the extended position by a spring 92. For example, spring 92 may be embodied as a coil spring having one end seated against an axially limited surface and an opposite end engaged against an underside of coupler element 90.

Docking station 14 may further comprise sensors for detecting operational information and transmitting the information to flush controller 84. Docking station 14 may have a proximity sensor 94 arranged to detect the presence of switchable flow valve 24 in valve seat 82. Proximity sensor 94 may be connected to flush controller 84 and may provide a proximity signal to the flush controller indicating that flow valve 24 is received by valve seat 82. In the illustrated embodiment, coupler element 90 may include a reflective surface 96, and proximity sensor 94 may be embodied as an optical proximity sensor arranged to emit light toward reflective surface 96 and detect a portion of the emitted light after reflection from reflective surface 96. As may be understood from FIG. 6, if switchable flow valve 24 is not received by valve seat 82, then coupler element 90 is biased by spring 92 to a default position wherein the flange portion 90B of coupler element 90 abuts with an upper interior surface of valve seat 82. When coupler element 90 is in the default position, reflective surface 96 is at its furthest distance from proximity sensor 94, such that proximity sensor 94 will register a lowest proximity signal value indicating no flow valve 24 is present. When switchable flow valve 24 is received by valve seat 82 but coupler element 90 and flow valve 24 are not in the single predetermined rotational orientation with respect to one another about valve switching axis 91, flow valve 24 forces coupler element 90 downward against the bias of spring 92 as shown in FIG. 10 into its retracted position. When coupler element 90 is in the retracted position, reflective surface 96 is at its closest distance from proximity sensor 94, such that proximity sensor 94 will register a highest proximity signal value indicating flow valve 24 is present but not mated with coupler element 90. When switchable flow valve 24 is received by valve seat 82, and coupler element 90 and flow valve 24 are in the single predetermined rotational orientation relative to one another about valve switching axis 91, coupler element 90 is urged upward by spring 92 to its extended position in mating engagement with flow valve 24 as shown in FIG. 11. When coupler element 90 is in the extended position, reflective surface 96 is at an intermediate distance from proximity sensor 94, such that proximity sensor 94 will register an intermediate signal value between the lowest and highest signal values. The intermediate proximity signal value indicates flow valve 24 is present in valve seat 82 and is mated with coupler element 90.

Proximity sensor 94 may be embodied by other types of proximity sensors, including but not limited to magnetic and capacitive proximity sensors.

Docking station 14 may have another sensor for measuring a rotational position of coupler element 90 about valve switching axis 91. For example, docking station 14 may comprise an optical encoder 98 connected to the flush controller 84, wherein the encoder measures a rotational position of coupler element 90 about the valve switching axis and provides a rotational position signal to the flush controller indicating the measured rotational position of the coupler element. For example, an encoder disc 100 may be connected to coupler element 90 for rotation about valve switching axis 91 in unison with coupler element 90, and optical encoder 98 may be arranged to detect the rotational position of encoder disc 100. In the embodiment shown, encoder disc 100 is connected to coupler element 90 by valve seat 82. As shown in the figures, valve seat 82 may include a plurality of legs 83 extending through openings 93 in coupler element 90 and into openings 101 in encoder disc 100. In the illustrated arrangement, valve seat 82 rotates with couple element 90 about valve switching axis 91, and conveys the rotational motion to encoder disc 100. The disclosure is not limited to the specific arrangement shown, and encoder disc 100 may be connected to coupler element 90 in other ways for conjoined rotation with the coupler element without straying from the disclosure. A magnetic encoder and corresponding encoder disc may be used in place of optical encoder 98 and encoder disc 100.

Flush controller 84, proximity sensor 94, and optical encoder 98 may be provided on a circuit board 102 mounted in a fixed position within the housing of docking station 14. An underside of encoder disc 100 may abut with an upper end of motor 88, thereby limiting movement of encoder disc 100 in a downward direction, and a top side of encoder disc 100 may be engaged by an end of spring 92.

As an alternative to using a second sensor or encoder 98 for measuring a rotational position of coupler element 90 about valve switching axis 91, proximity sensor 94 and reflective surface 96 may be adapted to perform this function. For example, reflective surface 96 may include a local feature (not shown) influencing reflected light detected by proximity sensor 94 when coupler element 90 is in a rotational position about valve switching axis 91 corresponding to the flush position of switchable flow valve 24, whereby the proximity signal indicates when switchable flow valve 24 is in the flush position. The local feature may be, for example, a gap, a light-absorbing region, or a light-dispersing region which attenuates the reflected light. Likewise, reflective surface 96 may include another local feature influencing reflected light detected by proximity sensor 94 when coupler element 90 is in a rotational position about valve switching axis 91 corresponding to the feed position of switchable flow valve 24, whereby the proximity signal indicates when switchable flow valve 24 is in the feed position.

Switchable flow valve 24 is shown in greater detail in FIGS. 12-15. Flow valve 24 may comprise a hollow valve housing 104 and a valve body 106 received by valve housing 104, wherein valve body 106 is rotatable about valve switching axis 91 relative to valve housing 104. Valve housing 104 may include a food entrance port 108 connectable to feed tubing branch 20, a flush entrance port 110 connectable to flush tubing branch 22, and an exit port 112 connectable to pump tubing portion 26. Valve body 106 may include a flow passage 114 having an input end 116 and an output end 118.

As shown in FIG. 14, valve body 106 may have a rotational feed position wherein the input end 116 of flow passage 114 faces the food entrance port 108 of valve housing 104 and the output end 118 of flow passage 114 faces the exit port 112 of valve housing 104 to enable flow communication between food entrance port 108 and exit port 112 through flow passage 114.

As illustrated in FIG. 15, valve body 106 may have a rotational flush position wherein the input end 116 of flow passage 114 faces the flush entrance port 110 of valve housing 104 and the output end 118 of flow passage 114 faces the exit port 112 of valve housing 104 to enable flow communication between flush entrance port 110 and exit port 112 through flow passage 114.

The rotational flush position of valve body 106 is angularly spaced from the rotational feed position of valve body 106 by a switching angle SA. The switching angle SA may be less than 90 degrees. In one embodiment, the switching angle is approximately 45 degrees.

Flow passage 114 may have a straight wall 120 extending linearly from input end 116 to output end 118, and a curved wall 122 diverging from straight wall 120 along a curved path from input end 116 to output end 118. A passage area (i.e. a cross-sectional area for flow) of output end 118 may be greater than a passage area of input end 116.

When flow valve 24 is in the feed position (FIG. 14), the disclosed configuration of flow valve 24 provides a straight flow path across the flow valve for nutritional liquid from nutritional liquid source 17. The configuration is advantageous for reducing stagnation of nutritional fluid as it passes through the flow valve and maintaining a steady delivery flow rate when pumping nutritional fluids of relatively high viscosity. When flow valve 24 is in the flush position (FIG. 15), the configuration of flow valve 24 provides a bent flow path across the flow valve for flushing liquid from flushing liquid source 18, which has a lower viscosity than the nutritional liquid and tends not to stagnate as the flow path changes direction through the flow valve. To the extent nutritional fluid may collect along curved wall 122 during pumping in the feed position, it will be flushed readily when flow valve 24 is switched to the flush position and flushing liquid is pumped through the flow valve.

Operation of docking station 14 in conjunction with enteral feeding pump 12 and an administration set 16 to perform a flush operation according to an embodiment of the disclosure is now described with reference to FIGS. 16 and 17.

FIG. 16 illustrates state transitions of pump 12 controlled though programming instructions executed by pump controller 56. The pump 12 may begin in a FlushIdle state 200. Pump controller 56 may command execution of a homing routine for flow valve 24 on docking station 14 with a Pump::HOME_VALVE command, described below with reference to FIG. 17, by which docking station 14 may determine the feed position and flush position of flow valve 24. From the FlushIdle state 200, pump 12 may transition to a Pumping state 210 characterized by operation of pumping mechanism 30. Within Pumping state 210, pump 12 may be in a Feeding substate 212 or a Flushing substate 214 depending upon whether flush valve 24 is in the feed position or the flush position. While pump 12 is in Pumping state 210, a user may enter a Pause instruction by means of user interface 64 to pause operation of pumping mechanism 30 and cause pump 12 to transition to a Paused state 220. The user may subsequently enter a Resume instruction by means of user interface 64 to cause pump 12 to transition from Paused state 220 back to Pumping state 210.

Based either on user input or a pump software program, pump controller 56 may initiate a feeding operation. Pump controller 56 may prepare for the feeding operation by sending a SET_VALVE_TO_FOOD command to flush controller 84 to switch flow valve 24 to its feed position or confirm that flow valve 24 is already in its feed position. Pump controller 56 may wait for a VALVE_SET_TO_FOOD signal from flush controller 84 before transitioning to Feeding substate 212. Once flow valve 24 is at the feed position, pump controller 56 may transition pump 12 to Feeding substate 212 by operating motor 62 such that pumping mechanism 30 delivers a desired volume of nutritional liquid to the user at a desired flow rate. As mentioned above, this pumping can be paused and resumed. When delivery of the programmed volume is completed, pump controller 56 may stop pumping mechanism 30 and pump 12 may transition back to FlushIdle state 200 and wait for another command.

The user or a pump software program may similarly command pump controller 56 to initiate a flushing operation. In this case, pump controller 56 may send a SET_VALVE_TO_FLUSH command to flush controller 84 to switch flow valve 24 to its flush position or confirm that flow valve 24 is already in its flush position. Pump controller 56 may wait for a VALVE_SET_TO_FLUSH signal from flush controller 84 before transitioning to Flushing substate 214. Once flow valve 24 is at the flush position, pump controller 56 may transition pump 12 to Flushing substate 214 by operating motor 62 such that pumping mechanism 30 delivers a desired volume of flushing liquid through administration set 16. As mentioned above, this pumping can be paused and resumed. When the programmed volume of flushing liquid has been pumped, pump controller 56 may stop pumping mechanism 30 and pump 12 may transition back to FlushIdle state 200 and wait for another command.

Reference is now made to FIG. 17 to describe state transitions associated with enteral feeding pump system 10 according to an embodiment of the present disclosure. Initially, enteral feeding pump system 10 is in a UserActions state 300 before administration set 16 is connected by the user to pump 12 and docking station 14. An initial SetUnloaded substate 310 indicates that cassette 28 is not yet loaded in pump 12 and flow valve 24 is not yet loaded in docking station 14. If the user first loads cassette 28 in pump 12, the substate transitions from SetUnloaded substate 310 to SetLoadedInPump substate 320. Subsequently, if the user loads flow valve 24 in valve seat 82, the substate transitions from SetLoadedInPump substate 320 to SetLoaded substate 340, indicating that administration set 16 is fully loaded and connected to pump 12 and docking station 14. Alternatively, if the user first loads flow valve 24 in valve seat 82, the substate transitions from SetUnloaded substate 310 to SetLoadedInValve substate 330. Subsequently, if the user loads cassette 28 in pump 12, the substate transitions from SetLoadedInValve substate 330 to SetLoaded substate 340. Thus, cassette 28 and flow valve 24 may be loaded in any order. Loading of cassette 28 in pump 12 may be confirmed by signals from set type detector 74 and door sensor 70 to pump controller 56. Loading of flow valve 24 in valve seat 28 may be confirmed by the proximity signal from proximity sensor 94 to flush controller 84. When the system is in SetLoaded substate 340, it is ready for a feeding operation or a flushing operation depending on the rotational position of flow valve 24.

Initially, docking station 14 may be in a ValveStateUnknown state 400 wherein valve actuator 86 is in an Idle substate 410 with electric motor 88 switched off, and the rotational position of flow valve 24 is unknown. When the user enters a START_FLUSH instruction to pump controller 56 by means of user interface 64 to initiate a flushing operation, pump controller 56 is configured to send a HOME_VALVE instruction to flush controller 84 of docking station 14 to switch electric motor 88 on and commence a Homing substate 420 for determining the position of flow valve 24. In Homing substate 420, the system enters a HomeToFlush substate in which motor 88 is commanded by flush controller 84 to rotate flow valve 24 about valve switching axis 91 until a FLUSH_POS_DETECTED signal is received from encoder 98 and/or proximity sensor 94 indicating that flow valve 24 is in the flush position. The system then enters a HomeToFood substate in which motor 88 is commanded by flush controller 84 to rotate flow valve 24 about valve switching axis 91 until a FOOD_POS_DE-TECTED signal is received from encoder 98 and/or proximity sensor 94 indicating that flow valve 24 is homed in the feed position. At this point, motor 88 is shut off and docking station 14 transitions to a ValveHomed state 500 and enters an AtFood substate 510. When docking station 14 is in the ValveHomed state 500, the position of flow valve 24 may be switched between the feed position and the flush position by issuing the SET_VALVE_TO FEED command and the SET_VALVE_TO_FLUSH command, respectively, as described above in connection with FIG. 16. Although the Homing routine described above sets flow valve 24 in the feed position as the homed position, the Homing routine may instead be programmed to set flow valve 24 in the flush position as the homed position.

Assuming flow valve 24 is homed at the feed position, pump controller 56 may issue the SET_VALVE_TO_FLUSH command to flush controller 84 as mentioned above, causing flush controller 84 to transmit a control signal to actuator 86 for switching flow valve 24 from the feed position to the flush position in response to the flush command. Docking station 14 transitions to a TurningToFlush substate 520 during which motor 88 is energized to rotate flow valve 24 until a FLUSH_POS_DETECTED signal is received from encoder 98 and/or proximity sensor 94 indicating that flow valve 24 is in the flush position. Docking station 14 then transitions to an AtFlush substate 530 wherein flow valve 24 is at the flush position and the system is ready for a flush operation. At this point, pumping mechanism motor 62 may be driven in accordance with Flushing substate 214 to cause flushing liquid to be pumped from flushing liquid source 18 sequentially through flush tubing branch 22, flow valve 24, and pump tubing portion 26 to flush away residual nutritional liquid in administration set 16. As described above in reference to FIG. 16, the flushing operation may continue until a predetermined volume of flushing liquid has been pumped through administration set 16, at which point pump controller 56 may automatically terminate the flushing operation by stopping operation of pumping mechanism 30. During the flushing operation, the user may pause or terminate the flushing operation by means of user interface 64.

Once flushing is terminated, pump controller 56 may issue a SET_VALVE_TO_FOOD command to flush controller 84, causing flush controller 84 to transmit a control signal to actuator 86 for switching flow valve 24 from the flush position to the feed position so that pump 12 is ready for a feeding operation. Docking station 14 transitions to a TurningToFeed substate 540 during which motor 88 is energized to rotate flow valve 24 until a FEED_POS_DE-TECTED signal is received from encoder 98 and/or proximity sensor 94 indicating that flow valve 24 is in the feed position. Consequently, docking station 14 returns to AtFood substate 510.

As will be appreciated from the present disclosure, enteral feeding pump 12 remains compact and mechanically simple in furtherance of a lightweight design for ambulatory use, yet automated flushing is available by way of docking station 14. Homing and orientation of flow valve 24 is performed automatically, making the system very easy to use.

While the disclosure describes exemplary embodiments, the detailed description is not intended to limit the scope of the disclosure to the particular forms set forth. The disclosure is intended to cover such alternatives, modifications and equivalents of the described embodiments as may be included within the scope of the appended claims.

What is claimed is:

1. A flow valve comprising:
   a hollow valve housing including a food entrance port, a flush entrance port, and an exit port;
   a valve body received by the valve housing, the valve body being rotatable about a valve axis relative to the valve housing, the valve body including a flow passage having an input end and an output end;
   the valve body having a rotational feed position wherein the input end of the flow passage faces the food entrance port and the output end of the flow passage faces the exit port to enable communication between the food entrance port and the exit port through the flow passage;
   the valve body having a rotational flush position wherein the input end of the flow passage faces the flush entrance port and the output end of the flow passage faces the exit port to enable communication between the flush entrance port and the exit port through the flow passage;
   wherein a passage area of the output end of the flow passage is greater than a passage area of the input end of the flow passage;
   wherein the flow passage has a straight wall extending linearly from the input end to the output end and a curved wall diverging from the straight wall along a curved path from the input end to the output end.

2. A flow valve comprising:
   a hollow valve housing including a food entrance port, a flush entrance port, and an exit port;
   a valve body received by the valve housing, the valve body being rotatble about a valve axis relative to the valve housing, the valve body including a flow passage having an input end and an output end;
   the valve body having a rotational feed position wherein the input end of the flow passage faces the food entrance port and the output end of the flow passage faces the exit port to enable communication between the food entrance port and the exit port through the flow passage;
   the valve body having a rotational flush position wherein the input end of the flow passage faces the flush entrance port and the output end of the flow passage faces the exit port to enable communication between the flush entrace port and the exit port through the flow passage;
   wherein a passage area of the output end of the flow passage is greater than a passage area of the input end of the flow passage;
   wherein the flow passage has a first wall extending linearly from the input end to the output end and a second wall curving away from the first wall at the output end.

* * * * *